United States Patent [19]

Paerels et al.

[11] Patent Number: 4,609,753
[45] Date of Patent: Sep. 2, 1986

[54] DIPHENYL ETHERS HAVING HERBICIDAL ACTIVITY

[75] Inventors: Gerard B. Paerels; Cornelis W. Raven, both of Weesp, Netherlands

[73] Assignee: Duphar International Research B.V., Weesp, Netherlands

[21] Appl. No.: 606,269

[22] Filed: May 2, 1984

[30] Foreign Application Priority Data

May 6, 1983 [NL] Netherlands ............... 8301605
May 6, 1983 [NL] Netherlands ............... 8301606
May 9, 1983 [NL] Netherlands ............... 8301634

[51] Int. Cl.$^4$ ............... C07C 143/67; C07C 143/90; A01N 41/00
[52] U.S. Cl. ............... 560/13; 71/103; 71/111; 260/401; 260/402; 560/16; 560/21; 562/430; 564/162; 564/163; 558/394
[58] Field of Search ............... 560/13, 21, 16; 71/103, 71/111; 260/402, 401, 465 E; 564/162, 163; 562/430

[56] References Cited

FOREIGN PATENT DOCUMENTS 0023392 2/1981 European Pat. Off. ............ 560/21
0072946 5/1982 Japan ............................ 560/21

*Primary Examiner*—Charles F. Warren
*Assistant Examiner*—E. A. Flaherty
*Attorney, Agent, or Firm*—Stevens, Davis, Miller & Mosher

[57] ABSTRACT

The invention relates to new diphenyl ethers of the general formula

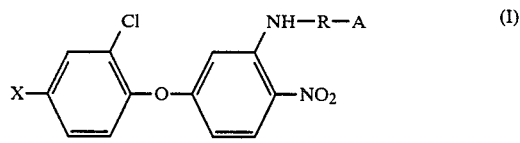

wherein
X is a trifluoromethyl group or an alkylsulphonyl group having 1–4 carbon atoms;
R is an alkylene or alkylidene group having 1–12 carbon atoms; and
A is a bis(alkoxyethoxy)phosphinyl group having 6–12 carbon atoms, a bis(alkoxyethoxyethoxy)phosphinyl group having 10–16 carbon atoms, a carboxy group, an alkenyloxycarbonyl group having 3–6 carbon atoms, an unsubstituted aminocarbonyl group, an N-alkylaminocarbonyl group having 2–5 carbon atoms, the alkyl group of which is substituted with a dialkylamino group having 2–4 carbon atoms, a cyano group, or an alkyloxycarbonyl group having 2–5 carbon atoms, the alkyl group of which may be substituted with an alkoxy, alkylthio or alkylsulphonyl group having 1–4 carbon atoms, with an alkoxyethoxy group having 3–6 carbon atoms, with a dialkylamino group having 2–4 carbon atoms, or with a hydroxyalkyldithio group having 2–4 carbon atoms;

with the provisos, that
(a) when X is a trifluoromethyl group and R is an alkylene or alkylidene group having 1–6 carbon atoms, then A is a bis(alkoxyethoxy)phosphinyl group, a bis(alkoxyethoxyethoxy)phosphinyl group, an N-alkylaminocarbonyl group, the alkyl group of which is substituted with a dialkylamino group, or an alkyloxycarbonyl group, the alkyl group of which is substituted with a dialkylamino group or a hydroxyalkyldithio group;
(b) when X is a trifluoromethyl group and R is an alkylene or alkylidene group having 8–12 carbon atoms, then A is a carboxy group, an unsubstituted alkoxycarbonyl group, an aminocarbonyl group, or a cyano group; and
(c) when X is an alkylsulphonyl group, then R is an alkylene or alkylidene group having 1–12 carbon atoms, and A is a carboxy group, an alkenyloxycarbonyl group, an unsubstituted or substituted alkyloxycarbonyl group, an aminocarbonyl group, or a cyano group.

The compounds have a herbicidal activity. After having been processed to compositions, the compounds may be used for controlling undesired plants in agricultural and herbicultural crop in a dosage from 0.01 to 5 kg of active substance per hectare.

3 Claims, No Drawings

DIPHENYL ETHERS HAVING HERBICIDAL ACTIVITY

The invention relates to new diphenyl ethers and to a method of preparing the new compounds The invention also relates to herbicidal compositions on the basis of the new compounds. The invention further relates to the use of these compositions for controlling undesired plants in agricultural and horticultural crops It is known that diphenyl ethers with a certain substitution pattern are suitable to control weeds in agricultural and horticultural crops. This control of weeds may take place after or before the emergence of the weeds; agents whose object it is to control the weed after the emergence thereof are termed post-emergence herbicides, the other ones are termed pre-emergence herbicides. For an unhindered growth of the crop during the whole growth period, both types of herbicides are used, if desired, but one single application is preferred, however, which, when a pre-emergence herbicide is used, usually is carried out simultaneously with or immediately after the sowing of the crop and, when a post-emergence herbicide is used, usually is carried out before the emerged weed starts hindering the growth of the crop. The advantage of the use of preemergence herbicides is that they can be provided in the soil destined for the crop simultaneously with the sowing of the crop; this is labour-saving, while damage to the standing crops upon application in a later stage is avoided. On the other hand, post-emergence herbicides are often more effectively active and can hence be used in smaller quantities to be able to effectively control the weed.

It stands to reason that in addition to the activity also the selectivity of the herbicide used is of the utmost importance. As a matter of fact , the undesired plants must be controlled, e.g. the growth of undesired plants must be suppressed, while the growth of the crop may not be detrimentally influenced by the herbicide used. An ideal herbicide must control the weed in the crop during the whole growth season after one single application in a small dosage. The herbicide should be capable not only of controlling all types of weeds, but also killing both the seedlings and full-grown plants of these weeds, as well as preventing the germination of the weed seeds. Nevertheless, the herbicide may not be phytotoxic with respect to the crops on which it is provided Of course, none of the herbicides now in use can equally meet these requirements and consequently is ideal. An effective weed control is usually associated with too large a phytotoxicity with respect to the crop, while a herbicide which has no detrimental influence whatsoever on the crop in a given dosage, does usually not control all weeds effectively in the same dosage. From the foregoing it may be clear, that small differences in herbicidal activity and in influence on the crop may already be very important in assessing the practical applicability of herbicides.

Chemically related diphenylethers are described in the non-prepublished Netherlands patent applications 8105047 and 8105220 in the name of the Applicant. Diphenyl ethers having herbicidal activity are known from the European patent application 27555, for example N-methyl-2-[N-(2-nitro-5-phenoxy-6-chloro)anilino] propionamide. As will become apparent from the examples, however, this compound has hardly any herbicidal activity in a dosage of 0.1 kg per hectare, usual for "post"-application. Further it has been proved, that under comparable conditions the activity, particularly against monocotyle weeds, of another chemically related substance, viz. methyl 2-[N-methyl-N-{2-nitro-5-(2-chloro-4-trifluoromethylphenoxy)phenyl}amino]-propionate, known from Chem. Abstracts 97,1982, 163488 g, leaves to be desired. Other chemically related diphenyl ether herbicides are described in the recently published European patent application 72348, e.g. methyl 3-[N-{2-nitro-5-(2-chloro-4-trifluoromethylphenoxy)phenyl}amino]-propionate. As will become apparent from the examples, however, the selectivity of the last-mentioned compound leaves to be desired.

It is the object of the invention to provide herbicides which can selectively control undesired plants in agricultural and horticultural crops, and simultaneously have an improved activity and/or selectivity as compared with the above-mentioned known compounds. This object can be achieved by new diphenyl ethers of the general formula

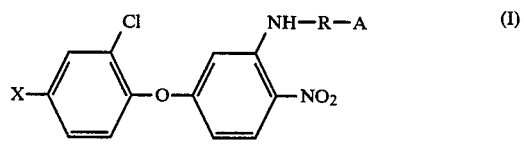

wherein
X is a trifluoromethyl group or an alkylsulphonyl group having 1–4 carbon atoms;
R is an alkylene or alkylidene group having 1–12 carbon atoms; and
A is a bis(alkoxyethoxy)phosphinyl group having 6–12 carbon atoms, a bis(alkoxyethoxyethoxy)phosphinyl group having 10–16 carbon atoms, a carboxy group, an alkenyloxycarbonyl group having 3–6 carbon atoms, an unsubstituted aminocarbonyl group, an N-alkylaminocarbonyl group having 2–5 carbon atoms, the alkyl group of which is substituted with a dialkylamino group having 2–4 carbon atoms, a cyano group, or an alkyloxycarbonyl group having 2–5 carbon atoms, the alkyl group of which may be substituted with an alkoxy, alkylthio or alkylsulphonyl group having 1–4 carbon atoms, with an alkoxyethoxy group having 3–6 carbon atoms, with a dialkylamino group having 2–4 carbon atoms, or with a hydroxyalkyldithio group having 2–4 carbon atoms; with the provisos, that (a) when X is a trifluoromethyl group and R is an alkylene or alkylidene group having 1–6 carbon atoms, then A is a bis(alkoxyethoxy)phosphinyl group, a bis(alkoxyethoxyethoxy)phosphinyl group, an N-alkylaminocarbonyl group, the alkyl group of which is substituted with a dialkylamino group, or an alkyloxycarbonyl group, the alkyl group of which is substituted with a dialkylamino group or a hydroxyalkyldithio group;

(b) when X is a trifluoromethyl group and R is an alkylene or alkylidene group having 8–12 carbon atoms, then A is a carboxy group, an unsubstituted alkoxycarbonyl group, an aminocarbonyl group, or a cyano group; and (c) when X is an alkylsulphonyl group, then R is an alkylene or alkylidene group having 1–12 carbon atoms, and A is a carboxy group, an alkenyloxycarbonyl group, an unsubstituted or substituted alkyloxycarbonyl group, an aminocarbonyl group, or a cyano group. Particularly suitable have been proved new compounds of the general formula

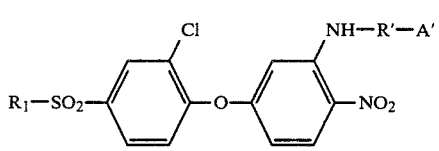

(II)

wherein
R₁ is an alkyl group having 1-4 carbon atoms,
R' is an alkylene or alkylidene group having 1-12 carbon atoms, and
A' is a carboxy group, an alkenyloxycarbonyl group having 3-6 carbon atoms, an aminocarbonyl group, a cyano group, or an alkyloxycarbonyl group having 2-5 carbon atoms, the alkyl group of which may be substituted with an alkoxy, alkylthio or alkylsulphonyl group having 1-4 carbon atoms or with an alkoxyethoxy group having 3-6 carbon atoms.

Examples of new diphenyl ethers according to the invention which may be used as selective herbicides are:

(1) methyl 11-[N-{2-nitro-5-(2-chloro-4-trifluoromethyl phenoxy)phenyl}amino]decanecarboxylate;
(2) 11-[N-{2-nitro-5-(2-chloro-4-trifluoromethylphenoxy) phenyl}amino]decanecarboxylic acid;
(3) bis(2-methoxyethyl) 1-[N-{2-nitro-5-(2-chloro-4-trifluoromethylphenoxy)phenyl}amino]ethanephosphonate;
(4) bis(2-ethoxyethyl) 1-[N-{2-nitro-5-(2-chloro-4-trifluoromethylphenoxy)phenyl}amino]ethanephosphonate;
(5) methyl 2-[N-{2-nitro-5-(2-chloro-4-methylsulphonylphenoxy)phenyl}amino]propionate;
(6) 3-[N-{2-nitro-5-(2-chloro-4-methylsulphonylphenoxy)phenyl}amino]propionamide;
(7) methyl 3-[N-{2-nitro-5-(2-chloro-4-methylsulphonylphenoxy)phenyl}amino]propionate;
(8) 3-[N-{2-nitro-5-(2-chloro-4-methylsulphonylphenoxy) phenyl}amino]butyronitrile;
(9) 3-[N-{2-nitro-5-(2-chloro-4-methylsulphonylphenoxy)phenyl}amino]propionitrile;
(10) 2-[N-{2-nitro-5-(2-ohloro-4-methylsulphonylphenoxy)phenyl}amino]propionic acid;
(11) allyl 2-[N-{2-nitro-5-(2-chloro-4-methylsulphonylphenoxy)phenyl}amino]propionate;
(12) 2-(2-methoxyethoxy)ethyl 2-[N-{2-nitro-5-(2-chloro-4-methylsulphonylphenoxy)phenyl}amino]propionate;
(13) 2-methoxyethyl 2-[N-{2-nitro-5-(2-chloro-4-methylsulphonylphenoxy)phenyl}amino]propionate;
(14) isopropyl 2-[N-{2-nitro-5-(2-chloro-4-methylsulphonyl phenoxy)phenyl}amino]propionate;
(15) isopropyl 4-[N-{2-nitro-5-(2-chloro-4-methylsulphonyl phenoxy)phenyl}[amino]butyrate;
(16) 2-methoxyethyl 4-[N-{2-nitro-5-(2-chloro-4-methylsulphonylphenoxy)phenyl}amino]butyrate;
(17) 4-[N-{2-nitro-5-(2-chloro-4-methylsulphonyl-phenoxy) phenyl}(amino]butyric acid;
(18) methyl 4-[N-{2-nitro-5-(2-chloro-4-methylsulphonylphenoxy)phenyl}(amino]butyrate;
(19) 2-methylthioethyl 2-[N-{2-nitro-5-(2-chloro-4-methylsulphonylphenoxy)phenyl}amino]propionate;
(20) 2-methylsulphonylethyl 2-[N-{2-nitro-5-(2-chloro-4methylsulphonylphenoxy)phenyl} amino]propionate;
(21') 3'-[N-{2-nitro-5-(2-chloro-4-methylsulphonylphenoxy)
(21) 3-[N-{phenyl(amino]propionic acid;
(22) isopropyl 3-[N-{2-nitro-5-(2-chloro-4-methylsulphonylphenoxy)phenyl}amino]propionate;
(23) allyl 3-[N-{2-nitro-5-(2-chloro-4-methylsulphonylphenoxy)phenyl}amino]propionate;
(24') 2'-methoxyethyl 3'[N-{2-nitro-5-(2-chloro-4-methylsulphonylphenoxy)phenyl}amino]propionate;
(25) 2-(2-methoxyethoxy)ethyl 3-[N-{2-nitro-5-(2-chloro-4-methylsulphonylphenoxy)phenyl}amino]propionate;
(26) 2-methylsulphonylethyl 3-[N-{12-nitro-5-(2-chloro-4-methylsulphonylphenoxy)phenyl}amino]propionate;
(27) 2-methoxyethyl 2-[N-{2-nitro-5-(2-chloro-4-isopropylsulphonylphenoxy)phenyl}amino]propionate;
(28) 2-(2-methoxyethoxy)ethyl 2-[N-{2-nitro-5-(2-chloro-4-isopropylsulphonylphenoxy)phenyl}amino]propionate;
(29) allyl 2-[N-{2-nitro-5-(2-chloro-4-isopropylsulphonylphenoxy)phenyl}amino]propionate;
(30) 2-methylthioethyl 3-[N-{2-nitro-5-(2-chloro-4-methylsulphonylphenoxy)phenyl}amino]propionate;
(31) methyl 2-[N-{2-nitro-5-(2-chloro-4-isopropylsulphonylphenoxy)phenyl}amino]propionate;
(32) 2-methylthioethyl 2-[N-{2-nitro-5-(2-chloro-4-isopropyl sulphonylphenoxy)phenyl}amino]propionate;
(33) 2-methylsulphonylethyl 2-[N-{2-nitro-5-(2chloro-4isopropylsulphonylphenoxy)phenyl}amino]propionate;
(34) 3-[N-{2-nitro-5-(2-chloro-4-isopropylsulphonylphenoxy)phenyl}amino]propionic acid
(35) methyl 3-[N-{2-nitro-5-(2-chloro-4-isopropylsulphonylphenoxy)phenyl}amino]propionate;
(36) isopropyl 3-[N-{2-nitro-5-(2-chloro-4-isopropylsulphonylphenoxy)phenyl}amino]propionate;
(37) allyl 3-[N-{2-nitro-5-(2-chloro-4-isopropylsulphonylphenoxy)phenyl}amino]propionate;
(38) 2-methylthioethyl 3-[N-{2-nitro-5-(2-chloro-4-isopropyl sulphonylphenoxy)phenyl}amino]propionate;yphenyl
(39) methyl 4-[N-{2-nitro-5-(2-chloro-4-isopropylsulphonylphenoxy)phenyl}amino]butyrate;
(40) 2-methoxyethyl 3-[N-{2-nitro-5-(2-chloro-4-isopropylsulphonylphenoxy)phenyl}amino]propionate;
(41) 2-(2-methoxyethoxy)ethyl 3-[N-{2-nitro-5-(2-chloro-4-isopropylsulphonylphenoxy)phenyl}amino]propionate;
(42) 4-[N-{2-nitro-5-(2-chloro-4-isopropylsulphonylphenoxy)phenyl}butyric acid;
(43) 3-[N-{2-nitro-5-(2-chloro-4-isopropylsulphonylphenoxy)phenyl}amino]butyronitrile;
(44) 3-[N-{2-nitro-5-(2-chloro-4-isopropylsulphonylphenoxy)phenyl}amino]propionitrile;

(45) 2-(N,N-diethylamino)ethyl 2-[N-{2-nitro-5-(2-chloro-4-trifluormethylphenoxy)phenyl}amino]-propionate;

(46) 3-(N,N-dimethylamino)propyl 2-[N-{2-nitro-5-(2-chloro-4-trifluoromethylphenoxy)phenyl-}amino propionate;

(47) 2-(2-hydroxyethyldithio)ethyl 2-[N-{2-nitro-5-(2-chloro-4-trifluoromethylphenoxy)phenyl-}amino]propionate;

(48) N-[2-(N,N-diethylamino)ethyl-2-[N-{2-nitro-5-(2-chloro-4-trifluoromethylphenoxy)phenyl-}amino]propionamide;

(49) N-[2-(N,N-diethylamino)ethyl-3-[N-{2-nitro-5-(2-chloro-4-trifluoromethylphenoxy)phenyl-}amino]propionamide;

(50) [1-methyl-2-(N,N-dimethylamino)]ethyl 2-[N-{2-nitro-5-(2-chloro-4-trifluoromethylphenoxy)-phenyl}amino]propionate; and

(51) 2-(2-hydroxyethyldithio)ethyl 3-[N-{2-nitro-5-(2-chloro-4-trifluoromethylphenoxy)phenyl-}amino]propionate.

The substances according to the invention may be used for the control of undesired plants in agricultural and horticultural crops. Although the new diphenyl ethers have an interesting pre-emergence herbicidal activity, what is most striking is their activity as post-emergence herbicides. Therefore, the compounds according to the invention may be used as post- and as pre-emergence herbicides. The new diphenyl ethers may be used for the control of monocotyle weeds, for example, *Poa annua* (annual bluegrass), *Avena fatua* (wild oat), *Alopecurus myosuroides* (blackgrass), *Panicum miliaceum* (millet) and *Echinochloa crusgalli* (barnyard grass), and of dicotyle weeds, for example, *Galinsoga parviflora* (small-flowered g.), *Galium aparine* (cleavers), *Chenopodium album* (common lambsquarters), *Polygonum convolvulus* (wild buckwheat), *Capsella bursa-pastoris* (shepherd's purse), *Stellaria media* (chickweed), *Senecio vulgaris* (common groundsel), *Veronica arvensis* (corn speedwell), *Matricaria maritima* (chamomile), *Amaranthus retroflexus* (redroot pigweed), *Solanum nigrum* (black nightshade), *Spergula arvensis* (corn spurrey), *Urtica dioica* (stinging nettle), *Polygonum aviculare* (knotgrass), *Silybum marianum* (milk thistle), *Xanthium pensylvanicum, Datura stramonium, Ipomoea muricata, Ipomoea hederacea, Ipomoea lacunosa, Cassia obtusifolia, Sida spinosa, Anoda cristata, Abutilon theophrasti* and *Portulaca oleracea* in various crops, such as in cereals, for example, wheat, rice, maize, oats and barley, in leguminosae, for example, bean, pea, soya, peanut and lucerne, and in pasture-land.

For practical use, the substances according to the invention are processed to compositions. In such compositions the active substance is mixed with solid carrier material, if desired in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents, pastes, dusting powders, dispersible powders, miscible oils, granules, pellets and aerosol compositions.

Dispersible powders, pastes and miscible oils are compositions in concentrate form which are diluted prior to or during use.

The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/-suspension, if desired in the presence of a binder, on granular carrier material, for example porous granules (for example pumice and attaclay), mineral non-porous granules (sand or ground marlow), organic granules (for example, dried coffee grounds, cut tobaccostems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates of alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution a dispersing agent, and if desired, a surface-active substance has been added. When diluting with water shortly before or during spraying, an aqueous dispersion of the active substance is then obtained.

An aerosol composition according to the invention is obtained in the usual manner by incorporation the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

In addition to the above-mentioned ingredients, the agents according to the invention may also contain other substances known for use in this type of agents. For example a lubricant, for example, calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Growth regulating and pesticidal compounds known per se may also be incorporated in the compositions according to the invention. As a result of this the activity spectrum of the composition is widened and synergism may occur. In addition foliar fertilizers may be present.

For use in such a combination composition are to be considered, in addition to insecticidal and acaricidal compounds known per se, the following known growth regulating and fungicidal compounds:

Growth requlators, for example 1. higher alcohols, for example, octanol and decanol;
2. lower esters of fatty acids;
3. ethylene-generators, for example, (2-chloroethyl)-phosphonic acid and 2-chloroethyl-tris(2-methoxyethoxy)silane;
4. nitrodiphenylethers;
5. substituted dinitroanilines, for example 2-chloro-N-ethyl-6-fluoro-N-[2,6-dinitro-4-(trifluoromethyl)-phenyl]benzenemethaneamine;
6. trifluoromethylsulphonylamino compounds;
7. piperidinederivatives;
8. benzylthiocarbamates, for example, benzyl N,N'-dipropylthiocarbamate;
9. phosphorothionoamidates and amidothionophosphonic acid esters;
10. benzoxazoles;

and furthermore: maleic hydrazide; 2,3,4,6-di-O-isopropylidene-α-xylo-2-hexulo-furanosonic acid-sodium; N,N-dimethylaminosuccinic acid; α-cyclopropyl-4-methoxy-α-(pyrimidin-5-yl)benzyl alcohol; 2-chloroethyltrimethyl ammonium; N,N-di(phosphonomethyl) glycine; 9-hydroxyfluorene-9-carboxylic acid (or ester); 2-chloro-9-hydroxyfluorene-9-carboxylic acid (or ester); N-1-naphthylphthalaminic acid; 2,3-dihydro-5,6-diphenyl-1,4-oxathiine; N-(3,4-dimethyl-3-cyclohexenyl)butylamine; and 3,5-dinitro-2,6-dimethyl-4-tert.-butylacetophenone; or mixtures of these compounds.

Fungicides, for example 1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole (-2) carbamates and 1,2-bis (3-alkoxycarbonyl-2-thiureido)benzene; and furthermore 2,4-dinitro-6-(2-octylphenyl-crotonate); 1-[bis(dimethylamino)phosphoryl]-3-phenyl-5-amino-1,2,4-triazole; N-trichloromethylthiophthalimide; N-trichloromethylthiotetrahydrophthalimide; N-(1,1,2,2-tetrachloroethylthio)-tetrahydrophthalimide; N-dichlorofluoromethylthio-N-phenyl-N,N'-dimethylsulphamide; tetrachloroisophthalonitrile; 2-(4'-thiazolyl)-benzimidazole; 5-butyl-2-ethylamino-6-methylpyrimidine-4-yl-dimethylsulphamate; 1-(4-chlorophenoxy)-3,3-dimethyl-1(1,2,4-triazole-1-yl)-2-butanone; α-(2-chlorophenyl)-α-(4-chlorophenyl)-5-pyrimidinemethanol; 1-(isopropylcarbamoyl)-3-(3,5-dichlorophenyl) hydantoin; N-(1,1,2,2-tetrachloroethylthio)-4-cyclohexene-1,2-carboximide; N-trichloromethylmercapto-4-cyclohexene-1,2-dicarboximide; N-tridecyl-2,6-dimethylmorpholine; metal salts of ethylphosphite; and N-(2,6-dimethylphenyl-N-methoxyacetyl)alanine methylester; or mixtures of these compounds.

The dosage of the composition according to the invention desired for practical application will, of course, depend on various factors, for example, field of application, active substance chosen, form of composition, nature and size of the weeds and the weather conditions.

In general it holds that favourable results are reached with a dosage which corresponds with 0.01 to 5 kg of active substance per hectare, preferably 0.1 to 3 kg per hectare.

It has been found that the herbicidal activity of the compositions according to the invention may increase considerably by using suitable adjuvants, for example, mineral oils and/or polyoxyethylene compounds, such as the mineral oils and surface-active substances mentioned in Netherlands Patent Application No. 7613453. Dependent on the application, the quantity of the adjuvant to be used may vary within wide limits and usually is between 10 and 10,000 ml per hectare.

The compounds according to the invention are new substances which can be prepared in a manner known per se for the synthesis of related compounds. So the new compounds which correspond with the general formula

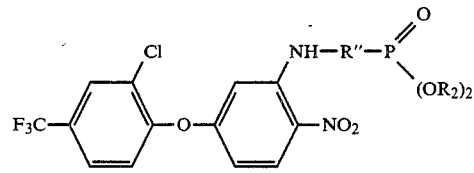

wherein
R'' is an alkylene or alkylidene group having 1–6 carbon atoms, and
$R_2$ is an alkoxyethyl group having 3–6 carbon atoms or an alkoxyethoxyethyl group having 5–8 carbon atoms, can be prepared by reacting a substituted aniline of the formula

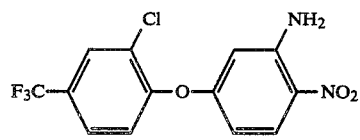

with an aliphatic aldehyde or ketone having 1–6 carbon atoms and with a phosphite of the general formula $P(OR_2)_3$ wherein $R_2$ has the above meaning. Instead of the above aliphatic aldehyde a polymerized aldehyde such as paraldehyde can be used.

A further surprising aspect of the invention is, that it has been found that the above reaction with aliphatic aldehyde and phosphite can best be carried out in an inert organic solvent, for example, an aromatic hydrocarbon, for example, toluene, in the presence of a catalytic quantity of a Lewis acid, preferably anhydrous ferric chloride or borontrifluoride, the latter for example in the form of an ether complex, e.g. borontrifluoride etherate The reaction is generally carried out at a temperature between room temperature and the boiling-point of the solvent used, preferably at the boiling-point of the solvent. The above reaction proceeds in a better yield than with an organic base, e.g. a tertiary amine, as the catalyst instead of a Lewis acid.

New compounds of the general formula

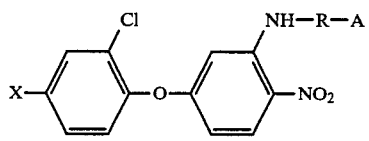

wherein the symbols have the meanings given before, can be prepared by reacting a compound of the general formula

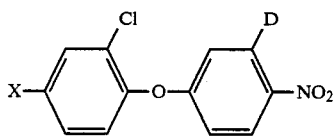

wherein
X has the above meaning, and
D is a halogen atom, a nitro group or an optionally substituted phenoxy group,
with an amino compound of the general formula

A—R—NH$_2$ wherein A and R have the above meanings, after which the resulting product, (a) if A is a carboxy group, if desired, is converted directly or via the corresponding acid chloride with an unsubstituted or substituted alkanol, an alkenol, ammonia, or a substituted alkylamine, a product being obtained of formula I, wherein A is an unsubstituted or substituted alkoxycarbonyl group, an alkenyloxycarbonyl group, an aminocarbonyl group, or a substituted alkylaminocarbonyl group, respectively, or (b) if A is an unsubstituted or substituted alkoxycarbonyl group, if desired, is converted with ammonia or a substituted alkylamine, a product being obtained of formula I, wherein A is an aminocarbonyl group or a substituted alkylaminocarbonyl group respectively.

If D in the starting material having the general formula III is a substituted phenoxy group, preferably for D a group is chosen having the general formula

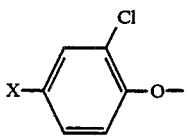

The above reaction between compound III and the amino compound is preferably carried out in an inert organic solvent, e.g. dimethyl formamide, acetonitrile, or an ether such as dioxane, at a reaction temperature between 0° C. and the boiling-point of the solvent used. A small amount of a suitable base, for example an alkali-metal hydroxide or -carbonate, may improve the reaction.

The direct esterification can be carried out in an excess of the substituted alkanol or alkenol, needed for the reaction, as a solvent. However, an inert polar organic solvent can also be used. Preferably this reaction is carried out under the influence of a little mineral acid at increased temperature. In the indirect esterification or amidation at first the carboxygroup is converted into the acid chloride with the aid of a substance suitable therefore, such as thionylchloride; after that the acid chloride is reacted with the alkanol, alkenol or amine, preferably in an inert organic solvent like acetonitrile, at room temperature or at a slightly increased temperature. The direct amidation reaction is preferably carried out in a polar organic solvent, for example an alcohol, at a reaction temperature between 0° C. and the boiling point of the solvent used.

The new compounds of the general formula

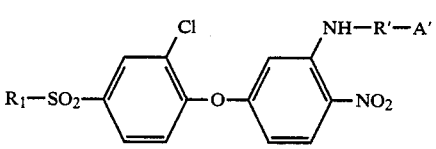

wherein the symbols have the above meanings, can also be prepared by reacting a compound of the general formula

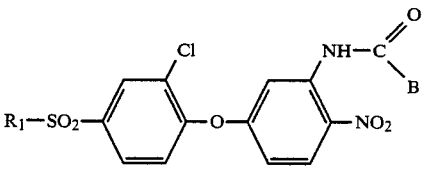

wherein
R$_1$ has the above meaning, and
B is a hydrogen atom, or a lower alkyl or alkoxy group,
with a compound of the general formula Hal—R'—A"

wherein
Hal is a halogen atom,
R' has the above meaning; and
A" is a cyano group or an alkyloxycarbonyl group having 2-5 carbon atoms, the alkyl group of which may be substituted with an alkoxy, alkylthio or alkylsulphonyl group having 1-4 carbon atoms or with an alkoxyethoxy group having 3-6 carbon atoms,
followed by a deacylation, after which the resulting product, if A" is a substituted or unsubstituted alkoxycarbonyl group, if desired, (a) is converted directly or via the corresponding acid chloride with ammonia, a product being obtained of formula II, wherein A' is an aminocarbonyl group, or (b) is hydrolyzed with an inorganic acid or base, a product being obtained of formula II, wherein A' is a carboxy group.

The first-mentioned reaction is usually carried out in two steps In the former reaction step the amino hydrogen atom is substituted by the group R'—A" while splitting off hydrogenhalide, while in the latter reaction step the group C(=O)B at the nitrogen atom is replaced by a hydrogen atom. Both reaction steps preferably take place in a polar organic solvent, the former, for example, in a dipolar aprotic solvent, such as dimethyl formamide, the latter, for example, in a protic solvent such as acetic acid. The former reaction step is preferably carried out under the influence of an acid binding substance, for example, an inorganic base such as potassium carbonate, the latter, for example, under the influence of a little acid, for example, hydrobromic acid. The hydrolysis reaction of the ester with an inorganic base or acid is preferably carried out in water, a polar organic solvent or a mixture thereof at a reaction temperature of 0°–50° C. The reaction of the resulting ester with ammonia is preferably carried out in an inert polar organic solvent, for example, an alcohol such as methanol or ethanol, at room temperature or a slightly elevated or reduced temperature.

The above compounds of the general formula II can also be prepared by oxidizing the corresponding thio compounds, having the formula

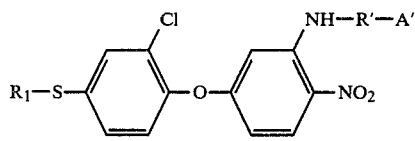

wherein the symbols have the above meanings. Suitable oxidizing agents are peroxy compounds, for example peroxycarboxylic acids like whether or not substituted perbenzoic acid. The reaction is preferably carried out in a polar organic solvent like a chlorinated hydrocarbon, e.g. chloroform, at room temperature or a slightly decreased temperature.

The same oxidation reaction can be used for converting compounds having the general formula II, wherein $R_1$ and R' have the meanings given before, and A' is an alkyloxycarbonyl group, the alkyl group of which is substituted with an alkylthio group, into the corresponding compounds, wherein A' represents an alkylsulphonyl subsituted alkyloxycarbonyl group. This oxidation reaction is also suitable for converting compounds having two alkylthio group in the desired corresponding compounds with two alkylsulphonyl groups.

The invention will now be described in greater detail with reference to the following specific examples.

EXAMPLE I

Preparation of 11-[N-{2-nitro-5-(2-chloro-4-trifluoromethylphenoxy)phenyl}amino]decanecarboxylic acid (2).

A mixture of 7.3 g of 3-chloro-4-(3,4-dinitrophenoxy)benzotrifluoride, 12.1 g of 11-aminodecanecarboxylic acid and 11.0 g of potassium carbonate in 100 ml of acetonitrile was refluxed for 24 hours. After evaporation of the solvent in vacuo the residue was dissolved in water. After extraction with diethylether the water layer was acidified with conc. hydrochloric acid and extracted with methylenechloride. After drying the solvent was evaporated from the organic phase in vacuo. The product obtained was purified with the aid of column chromatography ($SiO_2$, EtOAc). The desired product was obtained as a yellow crystalline material in a yield of 5.2 g; melting point 50° C.

EXAMPLE II

Preparation of methyl 11-[N-{2-nitro-5-(2-chloro-4-trifluoromethylphenoxy)phenyl}amino]decanecarboxylate (1).

An amount of 3.2 g of the acid (2), prepared according to Example I, dissolved in 30 ml of methanol, was refluxed for 3 hours in the presence of 1 ml of concentrated sulphuric acid. After the solvent had been partly evaporated in vacuo, methylenechloride was added. The solution was washed with water, aqueous bicarbonate solution and water successively, dried and evaporated in vacuo. The desired product was obtained as a yellow syrup in a yield of 3.1 g; $Rf(CHCl_3)$0,40.

EXAMPLE III

Preparation of methyl 3-[N-{2-nitro-5-(2-chloro-4-methylsulphonylphenoxy)phenyl}amino]propionate (7).

A mixture of 6.7 g of 2-chloro-4-methylsulphonyl-(3,4-dinitrophenoxy)benzene, 4.8 g of 3-aminopropionic acid and 9.9 g of potassium carbonate in 100 ml of acetonitrile was refluxed for 20 hours while stirring. After evaporation of the solvent water and ethylacetate were added. Then the mixture was stirred for 15 minutes, after which the water layer was separated and washed with ethyl acetate. After acidification with concentrated hydrochloric acid the product was extracted with methylenechloride. The organic layer was washed with water, filtered and reduced. 3-[N-{2-nitro-5-(2-chloro-4-methylsuphonylphenoxy)phenyl}amino]propionic acid was obtained as a glassy substance in a yield of 5.0 g. The carboxylic acid obtained, in an amount of 4.2 g was dissolved in 75 ml of methanol. After adding 2 ml of concentrated sulphuric acid the reaction mixture was refluxed for 1 hour. After purification as described in Example II the desired methyl ester (7) was obtained in a yield of 2.8 g; melting point 114° C.

The starting 3.4-dinitrophenoxy compound was prepared by a nitration of the corresponding 3-nitro compound with a mixture of potassium nitrate and conc. sulpuric acid Said 3-nitro compound was prepared by reacting 1.2-dichloro-4-methylsulphonylbenzene with 3-nitrophenol under the influence of a base, like potassium carbonate, in a suitable polar organic solvent, such as dimethyl sulphoxide.

In a corresponding manner the following compounds were prepared, the numbers correspond with the numbers used before in the specification.

| compound no. | physical data |
| --- | --- |
| 10 | m.p. 184° C. |
| 12 | Rf ($C_2H_5OC_2H_5$) 0.15 |
| 13 | Rf ($C_2H_5OC_2H_5$) 0.36 |
| 14 | Rf ($C_2H_5OC_2H_5$) 0.45 |
| 15 | Rf ($C_2H_5OC_2H_5$) 0.50 |
| 16 | Rf ($CH_3CO_2C_2H_5$) 0.60 |
| 17 | Rf ($CH_3CN$) 0.25 |
| 18 | m.p. 142° C. |
| 21 | Rf ($CH_3CO_2C_2H_5$) 0.25 |
| 22 | Rf ($C_2H_5OC_2H_5$) 0.33 |
| 24 | Rf ($C_2H_5OC_2H_5$) 0.23 |
| 25 | Rf ($CH_3CO_2C_2H_5$) 0.50 |
| 27 | Rf ($CH_2Cl_2$) 0.10 |
| 28 | Rf ($C_2H_5OC_2H_5$) 0.22 |

-continued

| compound no. | physical data |
| --- | --- |
| 31 | m.p. 94° C. |
| 34 | m.p. 144° C. |
| 35 | m.p. 122° C. |
| 36 | Rf ($C_2H_5OC_2H_5$) 0.36 |
| 39 | Rf ($C_2H_5OC_2H_5$) 0.42 |
| 40 | Rf ($C_2H_5OC_2H_5$) 0.28 |
| 41 | Rf ($C_2H_5OC_2H_5$) 0.15 |
| 42 | m.p. 140° C. |

EXAMPLE IV

Preparation of allyl 2-[N-{2-nitro-5-(2-chloro-4-methylsulphonylphenoxy)phenyl}amino]propionate (11).

The free acid (10), prepared according to Example III, in an amount of 4.15 g, was stirred at 50° C. for 3 hours, with 10 ml of thionylchloride. After evaporation at 50° C., addition of 20 ml of dry toluene and again evaporation at 50° C. the residue was dissolved in 20 ml of dry acetonitrile. This solution was added dropwise to 25 ml of allyl alcohol at room temperature; the mixture was stirred for 1 hour at 70° C. After evaporation, addition of toluene and evaporation again, the residue was dissolved in 20 ml of dry methylenechloride. After washing with aqueous bicarbonate and water the organic solution was filtered and evaporated, producing a syrup. Column chromatography yielded in 53% the desired product in a pure state (PMR); Rf($C_2H_5OC_2H_5$) 0.33.

In corresponding manner the following compounds were prepared; the numbers correspond again with the numbers used before in the specification.

| compound no. | physical data |
| --- | --- |
| 19 | Rf ($CH_3CO_2C_2H_5$) 0.65 |
| 23 | Rf ($CH_2Cl_2$) 0.10 |
| 29 | Rf ($CH_2Cl_2$) 0.28 |
| 30 | Rf ($CH_3CO_2C_2H_5$) 0.65 |
| 32 | Rf ($CH_2Cl_2$) 0.24 |
| 37 | Rf ($CH_2Cl_2$) 0.13 |
| 38 | Rf ($CH_2Cl_2$) 0.12 |
| 45 | $CH_3CO_2C_2H_5$ 0.20 |
| 46 | $CH_3CO_2C_2H_5$ 0.10 |
| 47 | $CH_3CO_2C_2H_5$ 0.70 |
| 50 | $CH_3CO_2C_2H_5$ 0.33 |
| 51 | $CH_3CO_2C_2H_5$ 0.65 |

In a corresponding manner compound No. 48 was prepared by reacting the acid chloride in question with N,N--diethyl-ethylenediamine in acetonitrile at 50° C.; m.p. 114° C.

EXAMPLE V

Preparation of methyl 2-[N-{2-nitro-5-(2-chloro-4-methylsulphonylphenoxy)phenyl}amino]propionate (5).

Methyl 2-[N-{2-nitro-5-(2-chloro-4-methylthiophenoxy)-phenyl}amino]propionate was prepared by reacting 2-chloro-4-methylthiophenol with 2-nitro-5-chloroacetanilide in dimethylsulphoxide at approx. 50° C. with the aid of $K_2CO_3$, followed by an alkylation with methyl 2-bromopropionate in dimethylformamide ($K_2CO_3$), and finally by a deacylation with a little HBr in acetic acid. This ester in an amount of 3.9 g was dissolved in 50 ml of absolute chloroform. To this solution was added slowly 4.9 g of 85% m-chloroperbenzoic acid under external cooling. The reaction mixture was stirred for 24 hours and then treated as described in Example II. After purification the desired product was obtained in a yield of 3.3 g; melting point 136° C.

In a corresponding manner compound no. 20 was prepared from thio compound no. 19, compound no. 26 from 2-methylthioethyl 3-[N-{2-nitro-5-(2-chloro-4-methylsulphonylphenoxy)phenyl}amino]propionate (prepared according to Example IV), and compound no. 33 from thio compound no. 32.

| compound no. | physical data |
| --- | --- |
| 20 | Rf ($CH_3CO_2C_2H_5$) 0.50 |
| 26 | m.p. 123° C. |
| 33 | Rf ($CH_3CO_2C_2H_5$) 0.50 |

EXAMPLE VI

Preparation of 3-[N-{2-nitro-5-(2-chloro-4-methylsulphonylphenoxy)phenyl}amino]propionamide (6).

The ester (7), obtained according to Example III, in an amount of 1.6 g was suspended in 40 ml of methanol. Ammonia was introduced until saturation and then the reaction mixture was stirred for two days. The solid material was sucked off and recrystallized from ethylacetate. The desired product was obtained in a yield of 0.9 g; melting point 196° C.

In a corresponding manner compound no. 49 was prepared from methyl 3-[N-{2-nitro-5-(2-chloro-4-trifluoromethylphenoxy)phenyl}amino]propionate and N,N-diethyl-ethylenediamine; m.p. 135° C.

EXAMPLE VII

Preparation of 3-[N-{2-nitro-5-(2-chloro-4-isopropylsulphonylphenoxy)phenyl}amino]butyronitrile (43).

A solution of 4.0 g of 2-chloro-4-isopropylsulphonyl-(3,4'-dinitrophenoxy)benzene and 2,5 g of 3-aminobutyronitrile in 30 ml of acetonitrile was refluxed for 13 hours. After evaporation the residue was recrystallized from methanol. The desired product was obtained in a yield of 3.3 g; m.p. 132° C.

EXAMPLE VIII

Preparation of 3-[N-{2-nitro-5-(2-chloro-4-isopropylsulphonylphenoxy)phenyl}amino]propionitrile (44).

A solution of 4.0 g of 2-chloro-4-isopropylsulphonyl-(3,4-dinitrophenoxy)benzene and 3.85 g of 3-aminopropionitrile. 0.5 fumarate in 100 ml of acetonitrile, to which 4.1 g of potassium carbonate was added, was refluxed for 6 hours. After evaporation the residue was dissolved in methylenechloride an extracted with water. After washing with water the organic layer was filtered and reduced. Recrystallisation from methanol yielded 3.0 g of the desired product; m.p. 140° C.

In a similar manner the following compounds were prepared; the numbers correspond again with the numbers used before in the specification.

| compound no. | physical data |
| --- | --- |
| 8 | Rf ($CH_3CO_2C_2H_5$) 0.70 |
| 9 | m.p. 166° C. |

EXAMPLE IX

Preparation of bis(2-methoxyethyl) 1-[N-{2-nitro-5-(2-chloro-4-trifluoromethylphenoxy)phenyl}amino]ethanephosphonate (3).

To a suspension of 2.3 g of 2-nitro-5-(2-chloro-4-trifluoromethylphenoxy)aniline in 40 ml of toluene were added 0.8 ml of acetaldehyde, 3.2 ml of tris(2-methoxyethyl)phophite and 0.3 ml of boriumtrifluoride-etherate. Under occasionally shaking the reaction mixture was heated during 1 hour on a steambath. After cooling, two successive washings with 25 ml of 2 N hydrochloric acid and water, and drying, the solvent was evaporated. The product obtained was purified with the aid of column chromatography (SiO$_2$; EtOAc). The desired product was obtained in a yield of 2.8 g; the product is syrupy; Rf (EtOAc) 0.25.

In a corresponding manner compound no. (4) was obtained; Rf (EtOAc) 0.35.

EXAMPLE X (a) Preparation of a solution of an active substance, namely methyl 2-[N-{2-nitro-5-(-2-chloro-4-methylsulphonylphenoxy)phenyl}amino]propionate (5), in a water-miscible liquid ("liquid"). 10. g of the above active substance were dissolved in a mixture of 10 ml of isophorone and approximately 70 ml of dimethylformamide, after which polyoxyethylene glycol ricinyl ether as an emulsifier was added in a quantitiy of 10 g. In a corresponding manner the other active substances were processed to 10% to 20% "liquids". In a corresponding manner, "liquids" were obtained in N-methyl pyrrolidone, dimethylformamide, and a mixture of N-methyl pyrrolidone and isophorone as solvents.

(b) Preparation of a solution of the active substance in an organic solvent. 200 mg of the active substance to be examined were dissolved in 1,000 ml of acetone in the presence of 1.6 g of nonylphenolpolyoxyethylene. This solution was used as a spraying liquid.

(c) Prepartion of an emulsifiable concentrate of the active substance. 10 g of the active substance to be examined were dissolved in a mixture of a polyoxyethylene sorbitan ester and an alkyl benzenesulphonate were added to this solution as an emulsifier.

(d) Preparation of a dispersible powder (W.P.) of the active substance. 25 g of the active substance to be examined were mixed with 68 g of kaolin in the presence of 2 g of sodium butylnaphthalene sulphonate and 5 g of lignine sulphonate.

(e) Preparation of a suspension concentrate (flowable) of the active substance. A mixture of 10 g of active substance, 2 g of lignine sulphonate and 0.8 g of a sodium alkyl sulphate was replenished with water up to a total quantity of 100 ml.

(f) Preparation of a granule of the active substance. 7.5 g of active substance, 5 g of sulphite lye and 87.5 g of ground dolomite were mixed, after which the resulting mixture was processed to a granular composition by means of the so-called compacting method.

EXAMPLE XI

Control of weeds ("post-emergence") in the glasshouse.

Compounds according to the invention were used in dosages of 100 g per hectare against the following weeds: *Galinsoga parviflora* (small-flowered g., Gp), *Chenopodium album* (common lambsquarters, Ca), and *Polygonum convolvulus* (wild buckwheat, Pc). After emergence the weeds were sprayed with a spraying liquid obtained according to Example X b with a suitable sprayer. The herbicidal activity was determined after two weeks. The damages to the weed plants in percentages are recorded in table A below. The known compound N-methyl-2-[N-(2-nitro-5-phenoxy-6-chloro)anilino]propionamide (a) was tested by comparison.

TABLE A

| compound no. | percentage damage on | | |
|---|---|---|---|
| | Pc | Gp | Ca |
| 1 | 90-100 | 90-100 | 90-100 |
| 2 | 90-100 | 90-100 | 90-100 |
| 3 | 90-100 | 90-100 | 90-100 |
| 4 | 90-100 | 90-100 | 90-100 |
| 5 | 90-100 | 90-100 | 90-100 |
| 7 | 90-100 | 90-100 | 90-100 |
| 8 | 90-100 | 90-100 | 90-100 |
| 9 | 90-100 | 90-100 | 90-100 |
| 10 | 90-100 | 90-100 | 90-100 |
| 11 | 90-100 | 90-100 | 90-100 |
| 12 | 90-100 | 90-100 | 90-100 |
| 13 | 90-100 | 90-100 | 90-100 |
| 14 | 90-100 | 90-100 | 90-100 |
| 15 | 90-100 | 90-100 | 90-100 |
| 16 | 90-100 | 90-100 | 90-100 |
| 17 | 90-100 | 90-100 | 90-100 |
| 18 | 90-100 | 90-100 | 90-100 |
| 19 | 90-100 | 90-100 | 90-100 |
| 20 | 90-100 | 90-100 | 90-100 |
| 21 | 90-100 | 90-100 | 90-100 |
| 22 | 90-100 | 90-100 | 90-100 |
| 23 | 90-100 | 90-100 | 90-100 |
| 24 | 90-100 | 90-100 | 90-100 |
| 25 | 90-100 | 90-100 | 90-100 |
| 26 | 90-100 | 90-100 | 90-100 |
| 27 | 90-100 | 90-100 | 90-100 |
| 28 | 90-100 | 90-100 | 90-100 |
| 29 | 90-100 | ca. 70 | 90-100 |
| 30 | 90-100 | 90-100 | 90-100 |
| 31 | ca 70 | 90-100 | 90-100 |
| 32 | 90-100 | 90-100 | 90-100 |
| 33 | ca. 70 | 90-100 | 90-100 |
| 34 | 90-100 | 90-100 | 90-100 |
| 35 | 90-100 | 90-100 | 90-100 |
| 36 | 90-100 | 90-100 | 90-100 |
| 37 | 90-100 | 90-100 | 90-100 |
| 38 | 90-100 | 90-100 | 90-100 |
| 39 | ca. 70 | 90-100 | 90-100 |
| 40 | 90-100 | 90-100 | 90-100 |
| 41 | 90-100 | 90-100 | 90-100 |
| 42 | 90-100 | 90-100 | 90-100 |
| 43 | 90-100 | 90-100 | 90-100 |
| 44 | ca. 70 | ca. 70 | 90-100 |
| 45 | 90-100 | 90-100 | 90-100 |
| 46 | 90-100 | 90-100 | 90-100 |
| 47 | 90-100 | 90-100 | 90-100 |
| 48 | 90-100 | 90-100 | 90-100 |
| 49 | 90-100 | ca. 70 | 90-100 |
| 50 | 90-100 | 90-100 | 90-100 |
| 51 | 90-100 | 90-100 | 90-100 |
| a, known | 0-10 | 0-10 | ca. 30 |

EXAMPLE XII

Control of weeds ("post-emergence") in the glasshouse.

In the same manner as described in Example XI compounds according to the invention in dosages of 30 g per hectare were tested on the weeds stated in Example XI, as well as on *Galium aparine* (cleavers, GA) and *Datura stramonium* (jimson weed, Ds). The results are recorded in Table B below.

TABLE B

| compound no. | percentage damage on | | | | |
|---|---|---|---|---|---|
| | Pc | Gp | Ca | Ga | Ds |
| 1 | 90-100 | 90-100 | 90-100 | ca. 70 | ca. 70 |
| 2 | 90-100 | 90-100 | 90-100 | 90-100 | 90-100 |
| 3 | 90-100 | 90-100 | 90-100 | 90-100 | 90-100 |
| 4 | 90-100 | 90-100 | 90-100 | 90-100 | 90-100 |
| 5 | 90-100 | 90-100 | 90-100 | 90-100 | 90-100 |

TABLE B-continued

| compound no. | percentage damage on | | | | |
|---|---|---|---|---|---|
| | Pc | Gp | Ca | Ga | Ds |
| 6 | 90-100 | 90-100 | 90-100 | 90-100 | 90-100 |
| 7 | 90-100 | 90-100 | 90-100 | 90-100 | 90-100 |
| 8 | 90-100 | 90-100 | 90-100 | 90-100 | 90-100 |
| 9 | 90-100 | 90-100 | 90-100 | 90-100 | ca. 70 |
| 10 | 90-100 | 90-100 | 90-100 | ca. 70 | 90-100 |
| 11 | 90-100 | 90-100 | 90-100 | 90-100 | 90-100 |
| 12 | 90-100 | 90-100 | 90-100 | ca. 70 | 90-100 |
| 13 | 90-100 | 90-100 | 90-100 | 90-100 | 90-100 |
| 14 | 90-100 | ca. 70 | 90-100 | ca. 70 | 90-100 |
| 15 | 90-100 | 90-100 | 90-100 | 90-100 | 90-100 |
| 16 | 90-100 | 90-100 | 90-100 | 90-100 | 90-100 |
| 17 | 90-100 | 90-100 | 90-100 | 90-100 | 90-100 |
| 18 | 90-100 | 90-100 | 90-100 | 90-100 | 90-100 |
| 19 | 90-100 | 90-100 | 90-100 | 90-100 | 90-100 |
| 20 | 90-100 | 90-100 | 90-100 | ca. 70 | 90-100 |
| 21 | 90-100 | 90-100 | 90-100 | 90-100 | 90-100 |
| 22 | 90-100 | 90-100 | 90-100 | 90-100 | 90-100 |
| 23 | 90-100 | 90-100 | 90-100 | 90-100 | 90-100 |
| 24 | 90-100 | 90-100 | 90-100 | 90-100 | 90-100 |
| 25 | 90-100 | 90-100 | 90-100 | 90-100 | 90-100 |
| 26 | 90-100 | 90-100 | 90-100 | 90-100 | 90-100 |
| 30 | 90-100 | 90-100 | 90-100 | 90-100 | 90-100 |

EXAMPLE XIII

Control of weeds ("post-emergence") in the glasshouse.

Compounds according to the invention in the dosages as stated in Table C below were tested on the following weeds: *Avena fatua* (wild oat, Af), *Alopecurus myosuroides* (blackgrass, Am) and *Panicum miliceum* (millet, Pm). The experiments were carried out in the same manner as described in Example XI. Ofter two weeks the damage to the weeds was determined: these damages are recorded in Table C. The known compound ethyl 2-[N-methyl-N- 2-nitro-5-(2-chloro-4-trifluoromethylphenoxy)phenyl amino]propionate (b) was tested by comparison.

TABLE C

| compound no. | dosage (g/ha) | percentage damage on | | |
|---|---|---|---|---|
| | | Af | Am | Pm |
| 2 | 30 | ca. 70 | ca. 30 | ca. 70 |
| 3 | 30 | ca. 70 | ca. 70 | ca. 70 |
| 7 | 30 | ca. 70 | ca. 70 | 90-100 |
| 10 | 100 | ca. 70 | ca. 70 | ca. 70 |
| 21 | 30 | ca. 30 | ca. 70 | 90-100 |
| 22 | 30 | ca. 70 | ca. 70 | ca. 70 |
| 23 | 30 | ca. 70 | ca. 70 | 90-100 |
| 24 | 30 | ca. 70 | ca. 70 | 90-100 |
| 25 | 30 | ca. 70 | ca. 70 | 90-100 |
| 26 | 30 | ca. 70 | ca. 70 | 90-100 |
| 30 | 30 | ca. 70 | ca. 70 | 90-100 |
| known (b) | 100 | ca. 30 | ca. 30 | ca. 30 |

EXAMPLE XIV

Selective control of various weeds ("post-emergence") in the glasshouse.

Compounds according to the invention in formulations as described in Example X b were tested in dosages of 100 g of active substance per hectare in the glasshouse on various weeds, viz. *Chenopodium album* (common lambsquarters), *Datura stramonium* (jimson weed), *Galium aparine* (cleavers), *Galingsoga parviflora* (small-flowered g) and *Polygonum convolvulus* (wild buckwheat). In addition the following crops were present: *Oryza sativa* (rice, Os) and *Triticum aestivum* (wheat, Ta). The experiments were carried out in the same manner as described in Example XI. After 3 weeks the damage to the plants was determined, the damage to the weeds being assessed as an average damage. The damages in percentage are recorded in Table D below. The known compound methyl 3-[N-{2-nitro-5-(2-chloro-4-trifluoromethylphenoxy)phenyl}amino]propionate (c) was tested by comparison.

TABLE D

| compound no. | percentage damage on | | |
|---|---|---|---|
| | weeds | Os | Ta |
| 1 | 100 | ca. 30 | 0-10 |
| 2 | 100 | ca. 30 | 0-10 |
| 4 | 100 | ca. 30 | 0-10 |
| 5 | 100 | ca. 30 | 0-10 |
| 8 | 100 | ca. 30 | 0-10 |
| 9 | 100 | ca. 30 | 0-10 |
| 10 | 100 | 0-10 | 0-10 |
| 11 | 100 | ca. 30 | 0-10 |
| 12 | 100 | ca. 30 | 0-10 |
| 13 | 100 | 0-10 | 0-10 |
| 14 | 93 | 0-10 | 0-10 |
| 15 | 100 | ca. 30 | 0-10 |
| 16 | 100 | 0-10 | 0-10 |
| 17 | 100 | 0-10 | 0-10 |
| 18 | 100 | 0-10 | 0-10 |
| 19 | 100 | 0-10 | 0-10 |
| 20 | 100 | 0-10 | 0-10 |
| 46 | 100 | ca. 30 | 0-10 |
| 47 | 87 | ca. 30 | 0-10 |
| 48 | 100 | ca. 30 | 0-10 |
| 49 | 93 | 0-10 | 0-10 |
| 51 | 100 | ca. 30 | 0-10 |
| known (c) | 100 | ca. 70 | ca. 70 |

EXAMPLE XV

Selective control of various weeds ("pre-emergence") in the glasshouse.

Compounds according to the invention were used in formulations according to Example X b in dosages of 1 kg of active substance per hectare against the weeds specified in Example XI; in the trial plots (soil) the following crops were sown: *Triticum aestivum* (wheat, Ta) and *Zea mays* (maize, Zm); the weeds and crops were sown simultaneously. Before emergence of the plants the plots were sprayed with the above formulations. After 3 weeks the activity of the herbicidal compositions was determined by assessing the damage in comparison with untreated plants, the damage to the weeds being assessed as an average damage. The damages in percentages are recorded in Table E below.

TABLE E

| compound no. | percentage damage on | | |
|---|---|---|---|
| | weeds | Ta | Zm |
| 11 | 89 | ca. 30 | ca. 30 |
| 12 | 89 | ca. 30 | ca. 30 |
| 13 | 78 | 0 | 0 |

In exactly the same manner other compounds according to the invention were tested in dosages of 300 g of active substance per hectare. The results are recorded in Table F.

TABLE F

| compound no. | percentage damage on | | |
|---|---|---|---|
| | weeds | Ta | Zm |
| 21 | 100 | 0 | 0 |
| 22 | 67 | 0 | 0 |
| 23 | 89 | ca. 30 | 0 |
| 24 | 78 | ca. 30 | 0 |
| 25 | 89 | ca. 30 | 0 |

TABLE F-continued

| compound no. | percentage damage on | | |
|---|---|---|---|
| | weeds | Ta | Zm |
| 30 | 89 | ca. 30 | 0 |

What is claimed is:

1. A diphenyl ether of the general formula

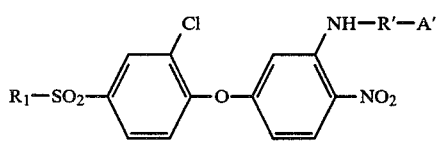

wherein $R_1$ is an alkyl group having 1–4 carbon atoms,

R' is an alkylene or alkylidene group having 1–12 carbon atoms, and

A' is a carboxy group, an alkenyloxycarbonyl group having 3–6 carbon atoms, an aminocarbonyl group, a cyano group, or an alkyloxycarbonyl group having 2–5 carbon atoms, the alkyl group of which may be substituted with an alkoxy, alkylthio or alkylsulphonyl group having 1–4 carbon atoms or with an alkoxyethoxy group having 3–6 carbon atoms.

2. A method of controlling undesired plants in agricultural and horticultural crop, characterized in that the crop or the soil destined for the crop is treated with a composition as claimed in claim 3 in a dosage from 0.01 to 5 kg of active substance per hectare, preferably from 0.1 to 3 kg per hectare.

3. A herbicidal composition comprising, in addition to a solid or liquid inert carrier material, a diphenyl ether as an active substance in a herbicidally effective amount, characterized in that the active substance is a compound of formula II, wherein the symbols have the meanings given in claim 1.

* * * * *